United States Patent
Harel et al.

Patent Number: 5,827,266
Date of Patent: Oct. 27, 1998

[54] SCANNER

[75] Inventors: Alex Harel, Savion; Yeshayahu Shai Eisenberg, Kiryat Tivon; Avigdor Shechter, Holon, all of Israel

[73] Assignee: Optomedic Medical Technologies, Ltd., Or-Yehuda, Israel

[21] Appl. No.: 724,079

[22] Filed: Sep. 30, 1996

[30] Foreign Application Priority Data

Oct. 1, 1995 [IL] Israel ........................................ 115477

[51] Int. Cl.$^6$ .................................................. A61B 17/36
[52] U.S. Cl. ............................................................ 606/13
[58] Field of Search ..................... 606/9, 10, 11, 606/12, 13, 15, 16, 17, 4, 5, 6

[56] References Cited

U.S. PATENT DOCUMENTS

| | | | |
|---|---|---|---|
| 3,643,015 | 2/1972 | Davidovits et al. ...................... | 178/6.8 |
| 4,728,770 | 3/1988 | Kaprelian ........................... | 219/121 LZ |
| 4,906,061 | 3/1990 | Yamaguchi . | |
| 5,009,233 | 4/1991 | Petrohilos ................................ | 128/666 |
| 5,219,347 | 6/1993 | Negus et al. ............................... | 606/17 |
| 5,262,884 | 11/1993 | Buchholz ................................ | 359/151 |
| 5,280,378 | 1/1994 | Lombardo ............................... | 359/199 |
| 5,374,817 | 12/1994 | Bard et al. ............................... | 235/462 |
| 5,391,165 | 2/1995 | Fountain et al. ............................ | 606/4 |
| 5,411,502 | 5/1995 | Zair ........................................... | 606/10 |
| 5,464,013 | 11/1995 | Lemelson ............................. | 606/10 X |
| 5,474,549 | 12/1995 | Ortiz et al. .................................. | 606/9 |
| 5,486,944 | 1/1996 | Bard et al. ................................ | 359/198 |
| 5,491,524 | 2/1996 | Hellmuth et al. ........................ | 351/212 |
| 5,493,109 | 2/1996 | Wei et al. ............................. | 606/10 X |
| 5,506,634 | 4/1996 | Wei et al. ................................. | 351/221 |
| 5,545,160 | 8/1996 | O'Rourke ................................. | 606/10 |

*Primary Examiner*—Jennifer Bahr
*Assistant Examiner*—Sonya Harris-Ogugua
*Attorney, Agent, or Firm*—Helfgott & Karas, P.C.

[57] ABSTRACT

A mirrorless scanner including a source of laser light producing a laser beam, a lens operative to receive the laser beam from the source of laser light and to direct it onto a target, and a vibrator coupled to the lens for vibrating the lens in at least two dimensions for causing the laser beam to scan across the target.

13 Claims, 14 Drawing Sheets

ന്ധം
SCANNER

FIELD OF THE INVENTION

The present invention relates to apparatus and methods for optical scanners generally, and particularly for scanners used with laser devices.

BACKGROUND OF THE INVENTION

The use of optical lasers to irradiate tissue is well known. Lasers may be used, for example, to ablate or vaporize tissue. It is well known to employ an optical scanner to control the distribution of the laser light, for example, to attain relatively short durations of laser light irradiating a given point on the tissue so that a desired portion of the tissue may be ablated at a controlled rate while other tissue is protected from possible damage.

Scanners which cause oscillatory motion of the laser light are known. U.S. Pat. No. 5,280,378 describes a medical laser system for scanning a beam of laser light which employs an oscillating mirror which repeatedly scans a laser beam in a cyclical pattern. U.S. Pat. No. 5,411,502 describes a scanning system which includes two mirrors each rotated by a motor. The mirrors are located with respect to each other and to a laser beam in such a manner so as to scan the laser beam cyclically along two orthogonal axes and to cause the beam to trace Lissajous figures over an area of tissue to be ablated.

As noted, both of the above mentioned systems employ mirrors which are moved in a cyclical manner to generate the desired scanning pattern. The use of mirrors has some drawbacks, however. For example, it may be difficult to provide a relatively compact scanning system, because space must be provided for mounting and moving the mirrors. In addition to the mirrors and mirror moving apparatus found in the scanning apparatus of the prior art, it is necessary to provide a lens for focusing the laser beam. Such a system may also be prone to malfunction due to misalignment of the mirrors with the laser beam source and/or a focusing lens. The addition of mirrors to the system tends to increase manufacturing costs and to reduce reliability.

SUMMARY OF THE INVENTION

The present invention seeks to provide a mirrorless scanning system which, inter alia, overcomes the above mentioned disadvantages of the prior art.

The present invention does not use mirrors in the scanning apparatus, but rather directly oscillates the focusing lens itself to produce the desired scanning pattern. Direct oscillation of the lens is simpler, more cost efficient and reliable than apparatus of the prior art and allows construction of a relatively compact scanning system.

The scanners of the present invention include resonant and non-resonant scanners. In the resonant scanner, the frequency of oscillation is determined by the natural frequency of the lens support structure with the lens mounted thereon. In the non-resonant scanner, the frequency of oscillation is determined by a driving force, such as produced by a solenoid or motor.

There is thus provided in accordance with a preferred embodiment of the present invention, a mirrorless scanner including a source of laser light producing a laser beam, a lens operative to receive the laser beam from the source of laser light and to direct it onto a target, and a vibrator coupled to the lens for vibrating the lens in at least two dimensions for causing the laser beam to scan across the target.

In accordance with a preferred embodiment of the present invention, the vibrator includes at least two electromagnetic vibration devices.

Additionally in accordance with a preferred embodiment of the present invention, the at least two electromagnetic vibration devices each provide vibration of the lens along a different axis.

Further in accordance with a preferred embodiment of the present invention, the vibrator is operative to vibrate the lens in a random or pseudorandom pattern.

Still further in accordance with a preferred embodiment of the present invention, the lens is mounted on a first one of the at least two electromagnetic vibration devices and the first one of the at least two electromagnetic vibration devices is mounted on a second one of the at least two electromagnetic vibration devices.

In accordance with a preferred embodiment of the present invention, the vibrator includes at least one electric motor.

Additionally, or alternatively, in accordance with a preferred embodiment of the present invention, the vibrator includes at least one solenoid.

In accordance with a preferred embodiment of the present invention, the lens is mounted on a flexure hinge.

There is also provided in accordance with a preferred embodiment of the present invention, a scanning method including the steps of producing a laser beam, employing a lens to receive the laser beam from the source of laser light and to direct it onto a target, and vibrating the lens in at least two dimensions for causing the laser beam to scan across the target.

In accordance with a preferred embodiment of the present invention, the vibrating step includes employing at least two electromagnetic vibration devices.

Additionally in accordance with a preferred embodiment of the present invention, the vibrating step includes vibration of the lens along two different axes.

The lens may be vibrated in a random or pseudorandom pattern.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1:
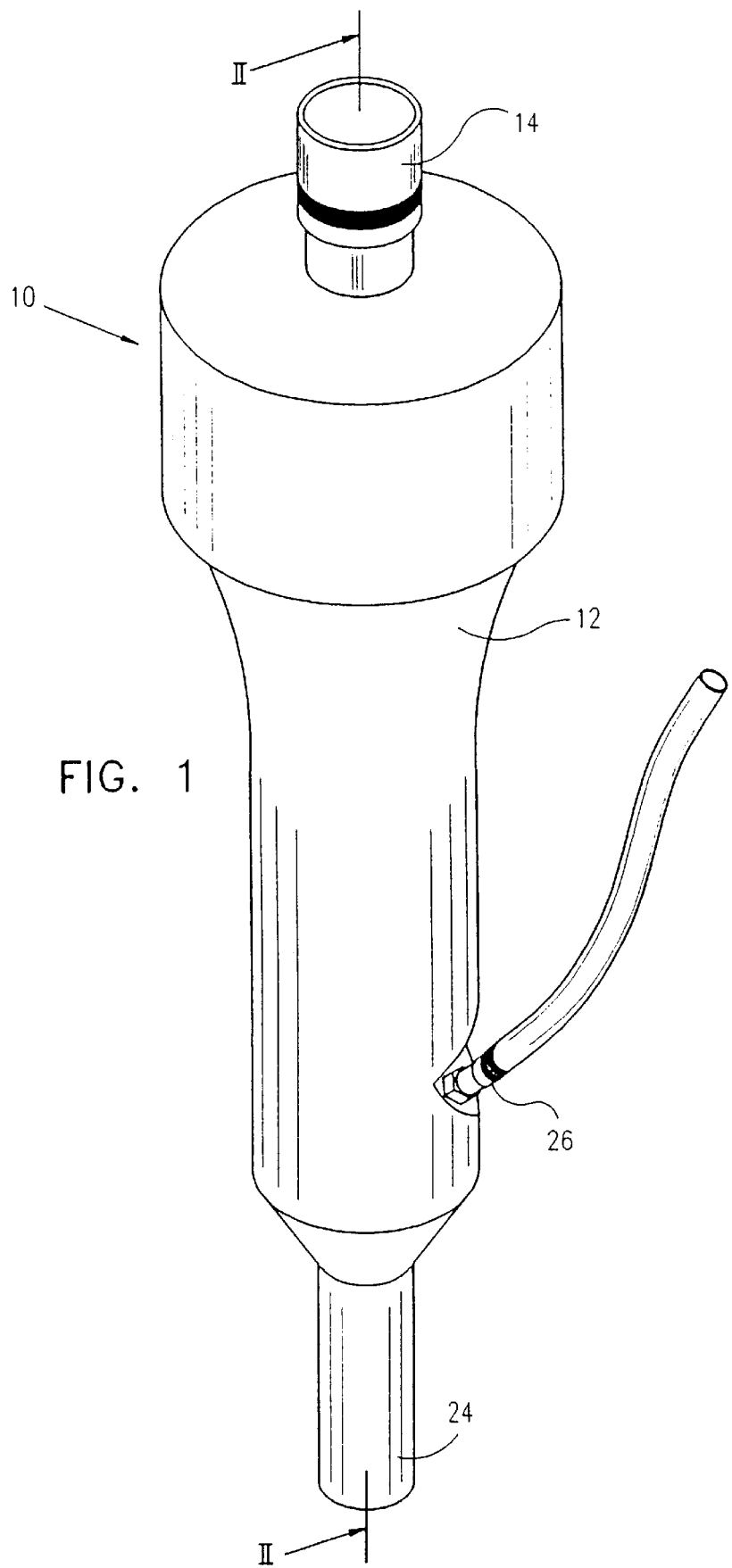
FIG. 1 is a simplified pictorial illustration of a mirrorless scanner, constructed and operative in accordance with a preferred embodiment of the present invention.

Reference is now made to FIG. 1 which illustrates a mirrorless scanner 10, constructed and operative in accordance with a preferred embodiment of the present invention. Scanner 10 preferably includes a housing 12, typically a hand piece, which is universally attachable, via a connector 14, to any suitable source of laser light (not shown), such as an articulated arm of a medical laser device.

Figure 2:
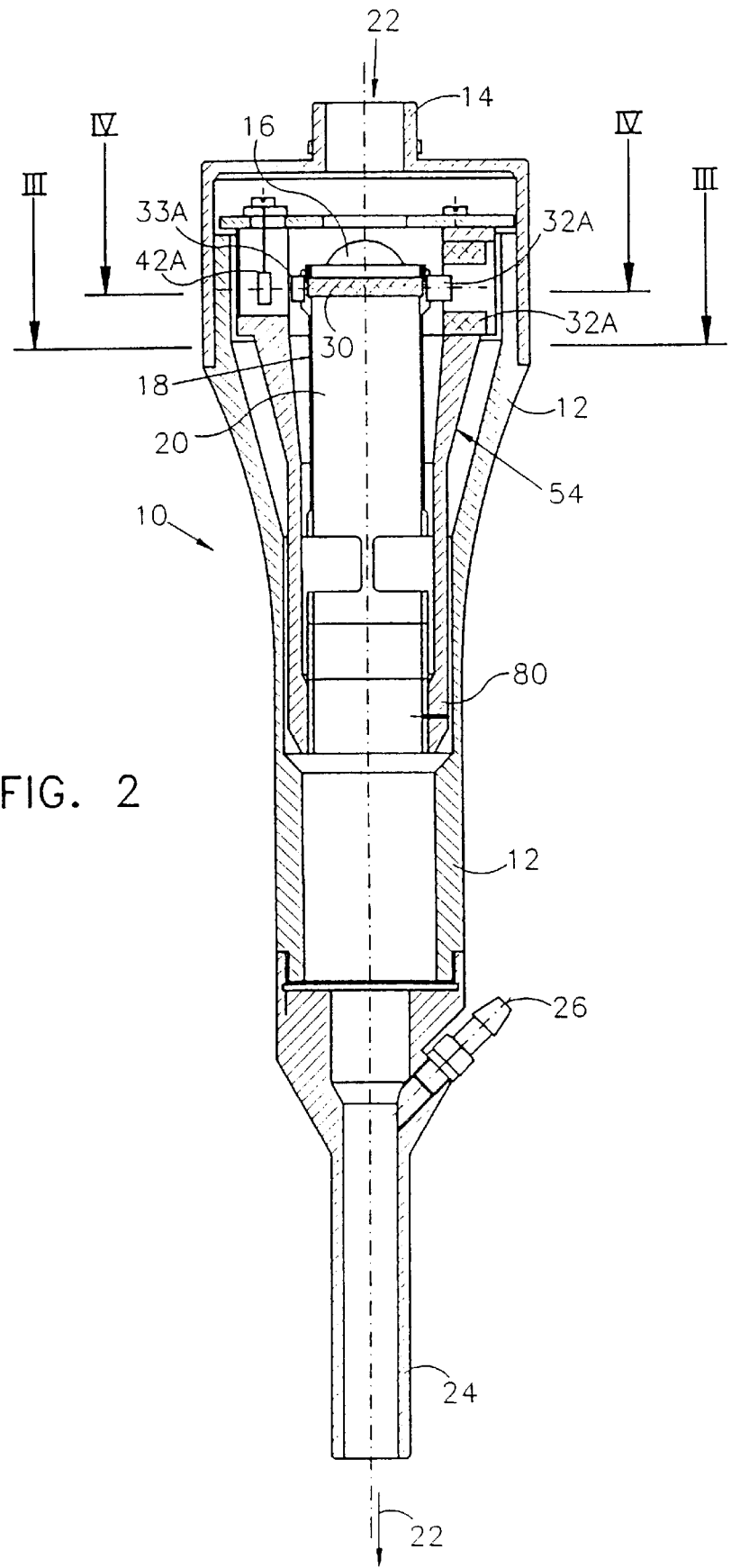
FIG. 2 is a simplified sectional illustration of the scanner of FIG. 1, taken along lines II—II in FIG. 1.

Referring to FIG. 2, it is seen that scanner 10 includes a lens 16 preferably fixedly attached to a lens support structure 18. In accordance with a preferred embodiment of the present invention, the lens support structure 18 includes a flexure hinge 20, preferably constructed of a resilient material and described in detail hereinbelow with reference to FIGS. 5A–5C. Connector 14 and lens 16 are arranged such that a laser beam (not shown) may be directed from a laser source (not shown), generally in a direction indicated by reference arrow 22, and be caused to pass through lens 16 and exit a tip 24 of housing 12, thereafter irradiating a target, such as a tissue (not shown).

Preferably a gas port 26 is provided upstream of tip 24 for flow therethrough of a gas such as air or nitrogen, which may help prevent debris from tissue ablation from entering and contaminating scanner 10.

Figure 4A:
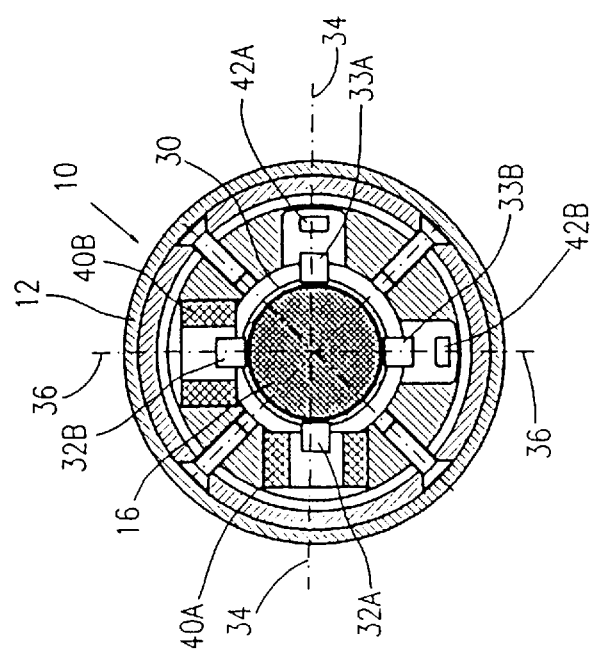
FIGS. 4A, 4B and 4C are simplified sectional illustrations of a portion of the scanner of FIG. 1, showing a lens in respective neutral orientation, displaced orientation generally along a first axis, and displaced orientation generally along a second axis, taken along lines IV—IV in FIG. 2.

Referring additionally to FIG. 4A, it is seen that a band 30 is preferably fixedly attached to the periphery of lens 16. Preferably a plurality of magnets 32A, 32B, 33A and 33B are fixedly attached to band 30. Magnets 32A, 32B, 33A and 33B are preferably generally equally spaced from each other along two generally mutually perpendicular axes 34 and 36, as seen in FIG. 4A.

Associated with each of axes 34 and 36, is an electromagnetic vibration device, such as electromagnets 40A and 40B, and corresponding control sensors, such as Hall effect sensors 42A and 42B. Electromagnets 40A and 40B are operative to apply a magnetic force to magnets 32A and 32B, respectively. The magnetic force may be attractive or repulsive and may be applied in the form of pulses. A magnetic force of sufficient magnitude may cause displacement of band 30 and lens 16 along any of axes 34 and 36 by virtue of the resiliency of lens support structure 18 and flexure hinge 20. The nature of the resiliency of flexure hinge 20 is described hereinbelow with reference to FIGS. 5A–5C.

Figure 4C:
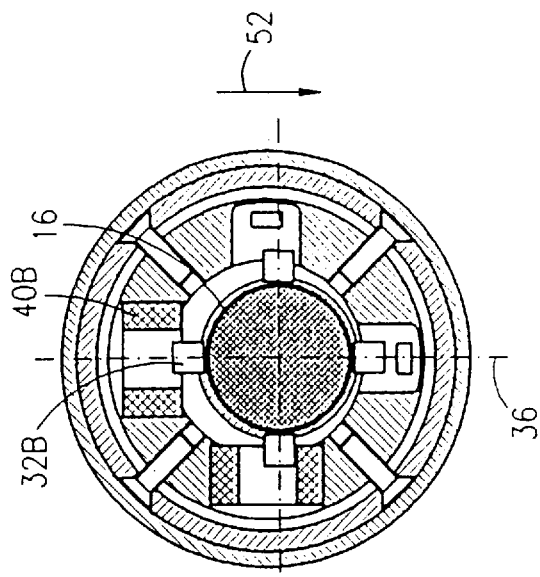
Figure 4B:
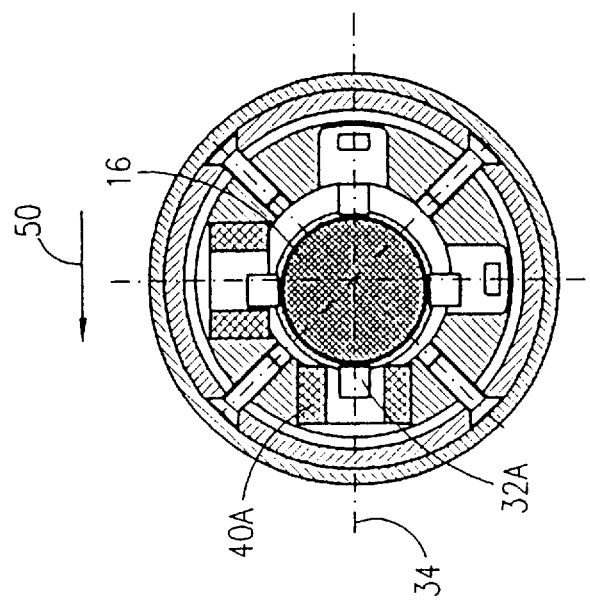

For example, application of a sufficient attractive magnetic force by electromagnet 40A on magnet 32A, causes lens 16 to displace in the direction of an arrow 50 along axis 34, as seen in FIG. 4B. In another example, application of a sufficient repulsive magnetic force by electromagnet 40B on magnet 32B, causes lens 16 to displace in the direction of an arrow 52 along axis 36, as seen in FIG. 4C.

Figure 3:
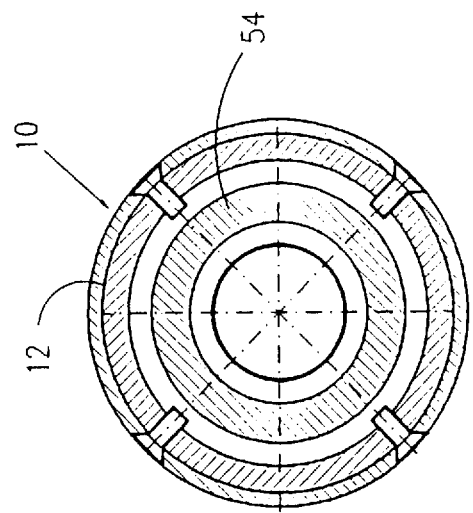
FIG. 3 is a simplified sectional illustration of a portion of the scanner of FIG. 1, showing support structure, taken along lines III—III in FIG. 2.

Magnets 40A and 40B and sensors 42A and 42B may be supported by a support assembly 54, as seen in FIGS. 2 and 3.

Figure 5A:
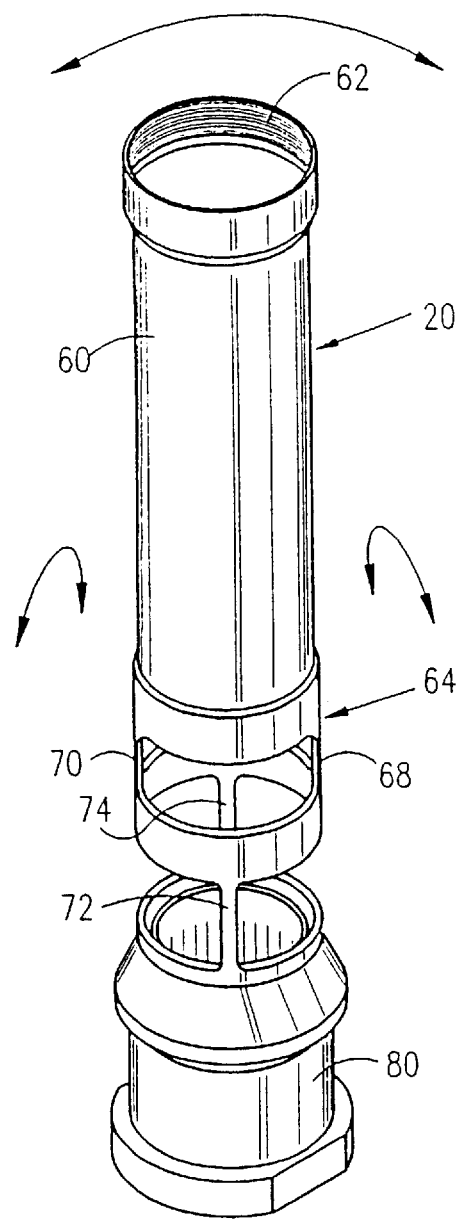
FIGS. 5A, 5B and 5C are simplified pictorial illustrations of a flexure hinge employed in the scanner of FIG. 1, shown in respective neutral orientation, displaced orientation generally along a first axis, and displaced orientation generally along a second axis.
Figure 5B:
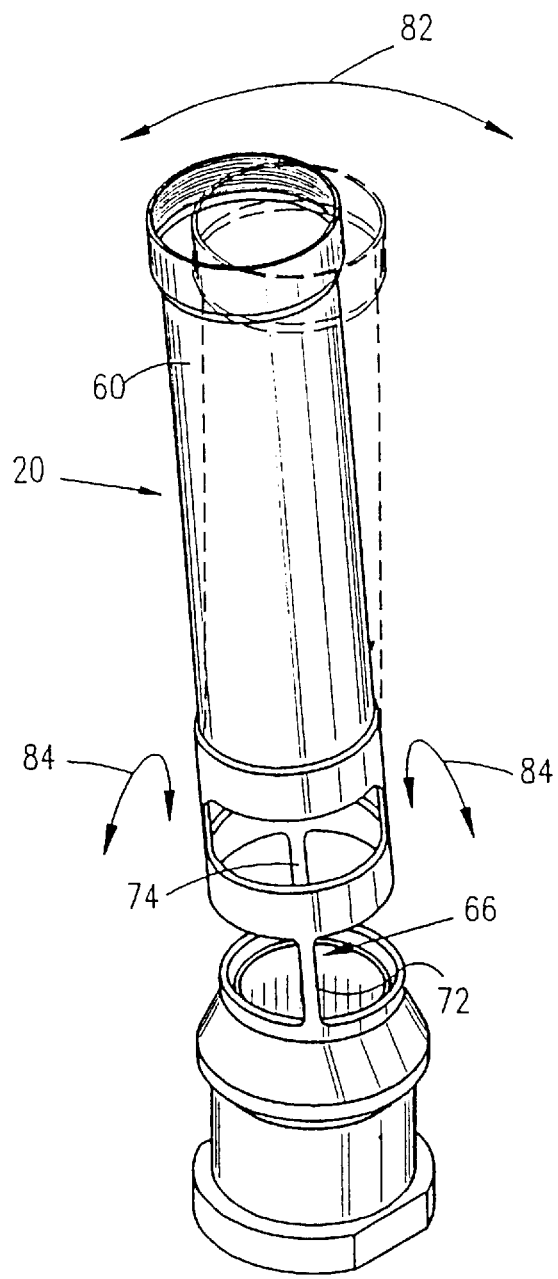
Figure 5C:
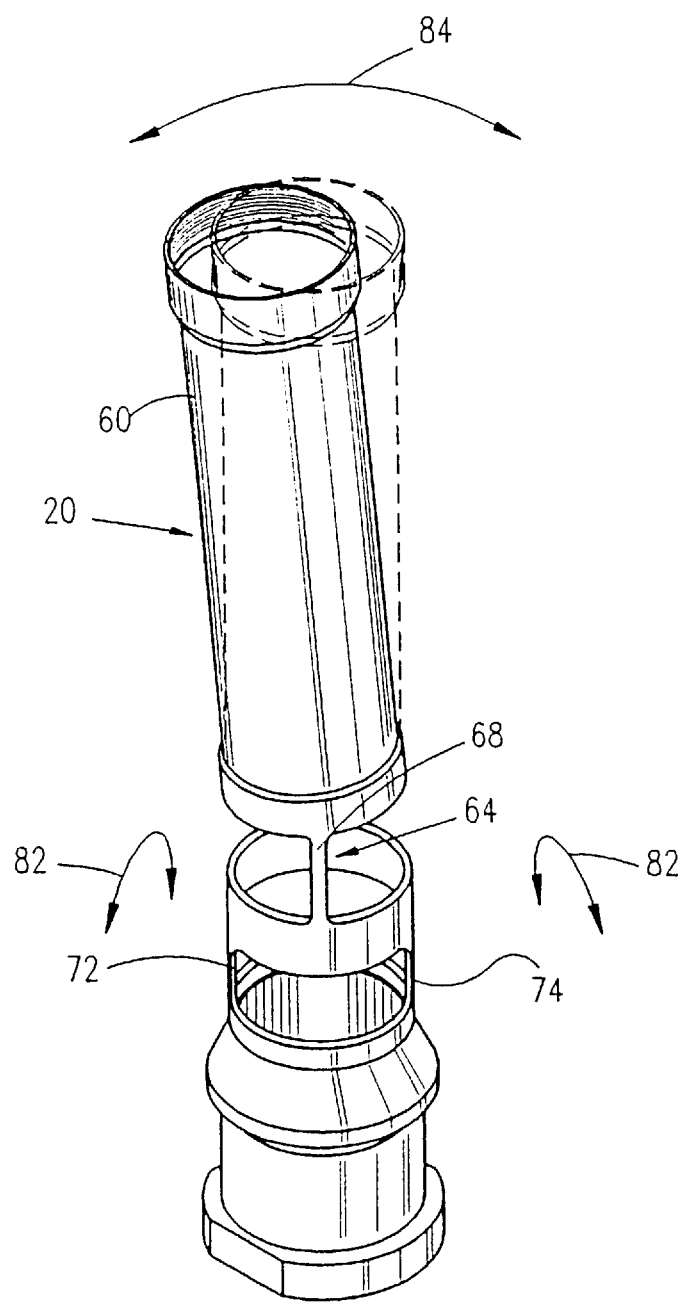

Reference is now made to FIGS. 5A–5C which illustrate flexure hinge 20. Flexure hinge 20 preferably comprises a tube 60 with a threaded end 62 for threaded attachment thereto of band 30, shown in FIGS. 2 and 4A. It is appreciated that band 30 may alternatively be attached to end 62 by any other suitable means, such as by bonding.

Attached to tube 60, at an end opposite to end 62, is a pair of generally mutually perpendicular flexure joints 64 and 66. Flexure joint 64 includes two slender arms 68 and 70, generally spaced 180 degrees apart. Flexure joint 66 includes two slender arms 72 and 74, generally spaced 180 degrees apart, and oriented generally 90 degrees from arms 68 and 70.

Flexure hinge 20 preferably includes a base 80 which may be fixedly attached to housing 12, as seen in FIG. 2.

Flexure hinge 20 has two principle resonant frequencies and associated modes of vibration. As seen in FIG. 5B, a first mode of vibration comprises a swaying motion about the base of flexure joint 66, generally along a direction indicated by a double arrow 82. The motion of lens 16 and band 30 along axis 34, shown in FIG. 4B, corresponds to the swaying motion of flexure hinge 20 shown in FIG. 5B.

As seen in FIG. 5C, a second mode of vibration comprises a swaying motion about the base of flexure joint 64, generally along a direction indicated by a double arrow 84, generally perpendicular to double arrow 82. The motion of lens 16 and band 30 along axis 36, shown in FIG. 4C, corresponds to the swaying motion of flexure hinge 20 shown in FIG. 5C.

It is noted that scanner 10 may operate as a resonant scanner, that is, the frequency of oscillation is determined by the natural frequency of lens support structure 18 with lens 16 mounted thereon. Alternatively, scanner 10 may operate as a non-resonant scanner, wherein the frequency of oscillation is determined by a driving force, such as produced by a solenoid or motor.

The oscillating motion of lens 16 determines the scanning pattern of a laser beam passing therethrough. A combination of two generally harmonic motions of lens 16 along the generally mutually perpendicular axes 34 and 36, by definition traces out a Lissajous figure. It is appreciated that the harmonic motion of lens 16 along axis 34 is independent of the harmonic motion of lens 16 along axis 36, and that the natural frequencies associated with motion along the axes 34 and 36 are generally unequal. In general, one or both of these natural frequencies is an irrational number, which means that an open Lissajous curve is traced. An open Lissajous curve is one which does not repeat its pattern. The importance of an open Lissajous curve will be discussed with reference to FIGS. 6A–6C.

Figure 6B:
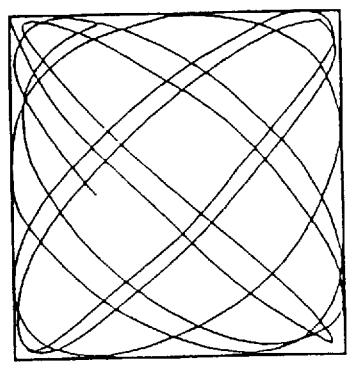
FIGS. 6A, 6B and 6C are simplified pictorial illustrations of a scanning pattern, generally shaped as open Lissajous curves, in respective first, second and third stages of progressive development.
Figure 6C:
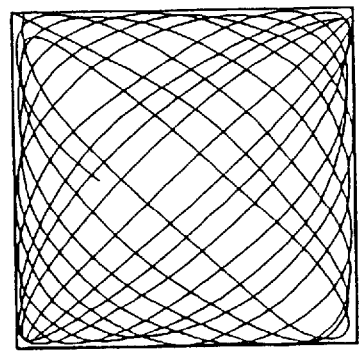
Figure 6A:
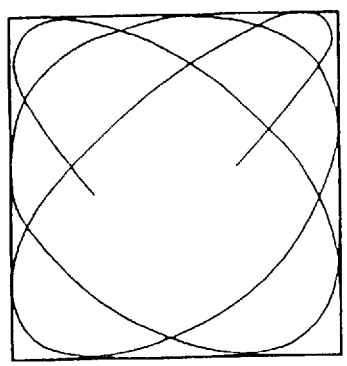

Referring to FIGS. 6A–6C, it is seen that repetitive formations of Lissajous figures may substantially uniformly irradiate an area of tissue. Typically, an area of tissue about 4 mm in length and width may be irradiated with an energy density of at least 40 mJ per square millimeter. Although a Lissajous curve which eventually repeats itself may be used to irradiate the desired area of tissue, an open Lissajous curve may be more efficient for substantially uniform irradiation of the tissue.

Figure 7:
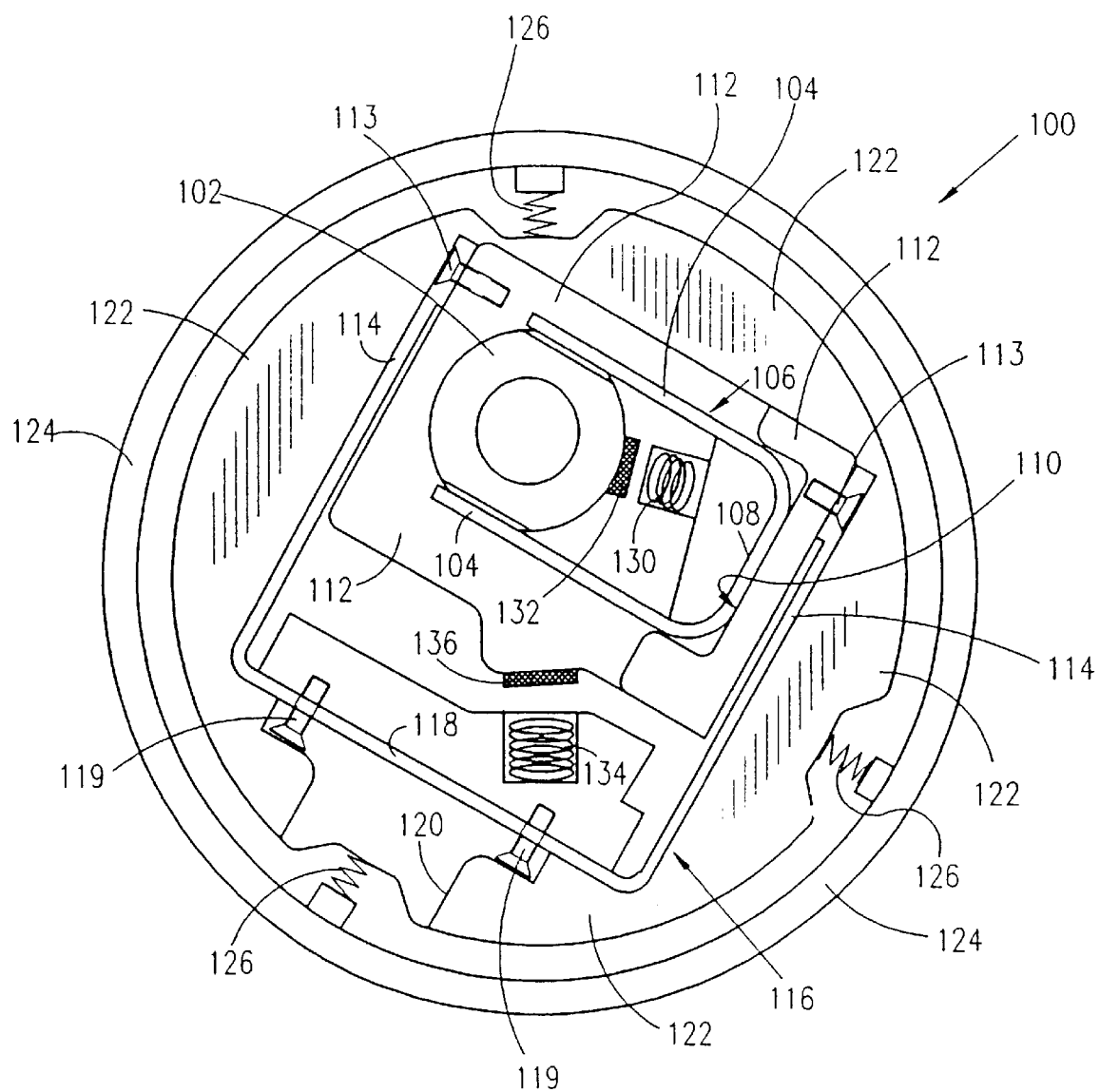
FIGS. 7 and 8 are partial, simplified pictorial illustrations of a mirrorless scanner, constructed and operative in accordance with another preferred embodiment of the present invention, in respective stationary and oscillating orientations.

Reference is now made to FIG. 7 which is a partial, simplified illustration of a mirrorless scanner 100, constructed and operative in accordance with another preferred embodiment of the present invention. Scanner 100 includes a lens 102 preferably fixedly attached, such as by bonding, to two tines 104 of a first flexural fork 106. A base 108 of first flexural fork 106 is preferably fixedly attached, such as by bonding, to a recessed area 110 formed in a generally rectangular frame 112.

Frame 112 is preferably fixedly attached, such as with screws 113, to two tines 114 of a second flexural fork 116. A base 118 of second flexural fork 116 is preferably fixedly attached, such as with screws 119, to a recessed portion 120 formed in a generally circular inner housing 122.

Inner housing 122 is preferably disposed inside an outer housing 124. Preferably a plurality of shock absorbing or damping elements, such as springs 126, substantially isolate shock and vibration of inner housing 122 from being transmitted to outer housing 124. Outer housing 124 may be similar in shape and construction to housing 12 described hereinabove with reference to FIGS. 1 and 2.

A first electromagnetic vibration device, such as a solenoid 130, is preferably attached to frame 112 and is operative to attract or repel a magnet 132, preferably fixedly attached to lens 102.

A second electromagnetic vibration device, such as a solenoid 134, is preferably attached to recessed portion 120 and is operative to attract or repel a magnet 136, preferably fixedly attached to frame 112.

Figure 8:
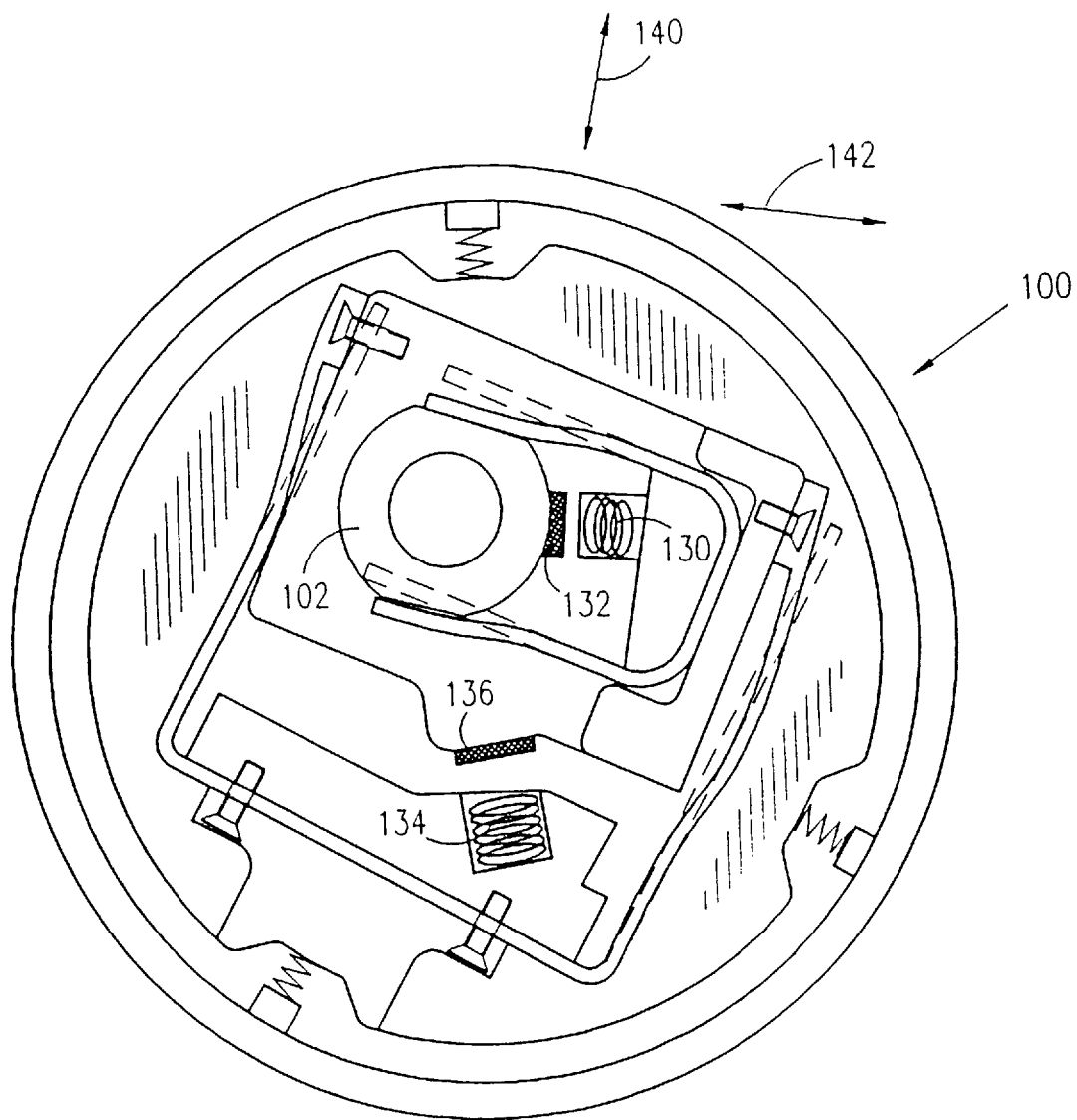

As seen in FIG. 8, the attractive and repulsive magnetic forces caused by solenoids 130 and 134 on magnets 132 and 136 respectively, cause lens 102 to oscillate along one or both of generally mutually perpendicular axes 140 and 142. A laser beam (not shown) passing through lens 102 is deflected according to the oscillations of lens 102, much in the same manner as described hereinabove for scanner 10 with reference to FIGS. 1–5C. The combination of the two generally harmonic motions of lens 102 along the generally mutually perpendicular axes 140 and 142, traces out a Lissajous figure, much in the same manner as described hereinabove with reference to FIGS. 6A–6C.

Figure 9:
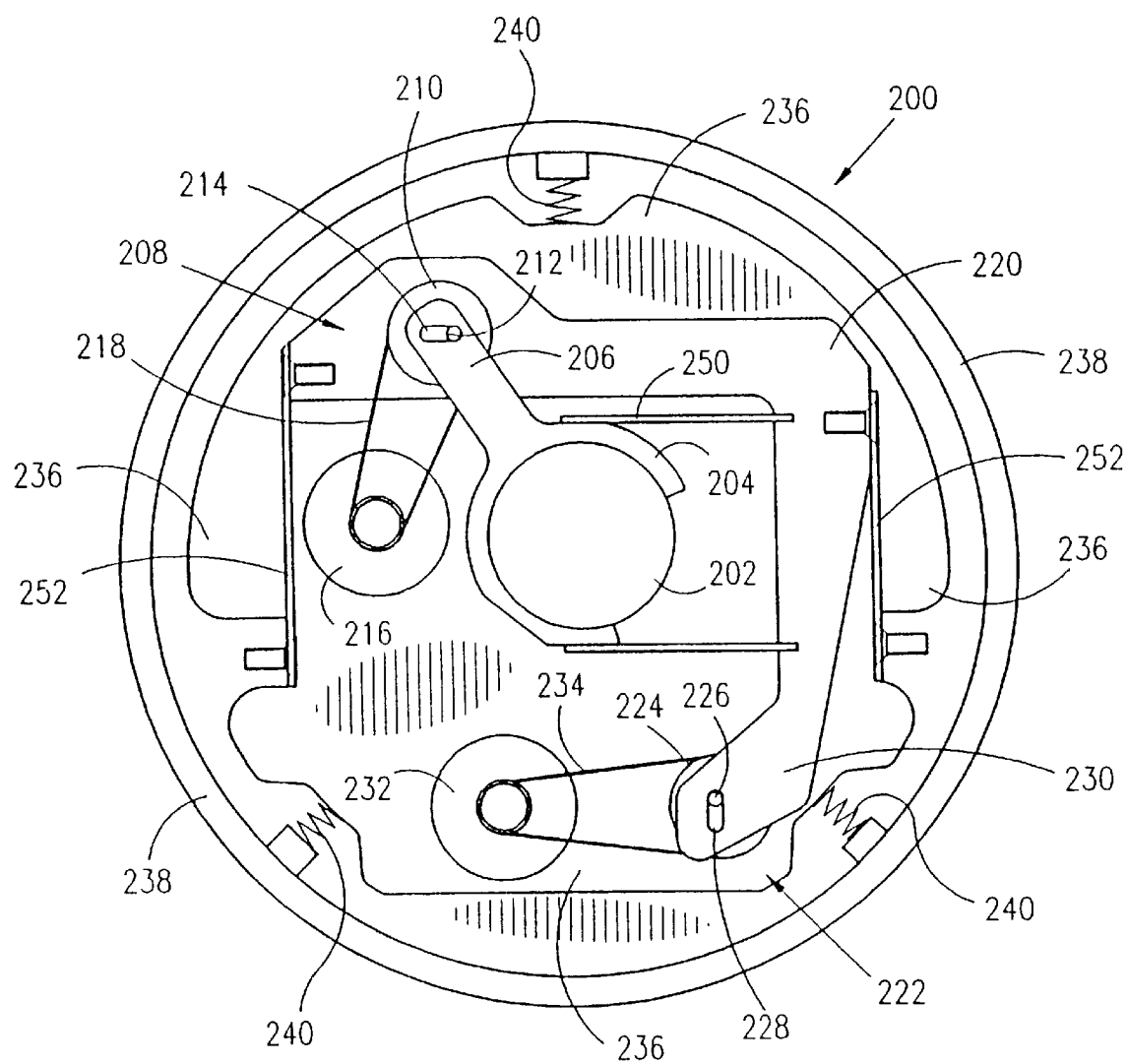
FIGS. 9 and 10 are partial, simplified pictorial illustrations of a mirrorless scanner, constructed and operative in accordance with yet another preferred embodiment of the present invention, in respective stationary and oscillating orientations.

Reference is now made to FIG. 9 which is a partial, simplified illustration of a mirrorless scanner 200, constructed and operative in accordance with another preferred embodiment of the present invention. Scanner 200 includes a lens 202 preferably fixedly attached, such as by bonding, to a first yoke 204. A base 206 of first yoke 204 is preferably pivotally attached to a first eccentric drive 208.

First eccentric drive 208 preferably includes a wheel 210 provided with an eccentric pin 212. Pin 212 communicates with an elongate slot 214 formed in base 206 of first yoke 204. A motor 216 is operatively connected to wheel 210 by means of a drive belt 218.

Wheel 210 is rotatably attached to a second yoke 220. Second yoke 220 is preferably pivotally attached to a second eccentric drive 222.

Second eccentric drive 222 preferably includes a wheel 224 provided with an eccentric pin 226. Pin 226 communicates with an elongate slot 228 formed in a base 230 of second yoke 220. A motor 232 is operatively connected to wheel 224 by means of a drive belt 234.

Motors 216 and 232 are preferably mounted in an inner housing 236. Inner housing 236 is preferably disposed inside an outer housing 238. Preferably a plurality of shock absorbing or damping elements, such as springs 240, substantially isolate shock and vibration of inner housing 236 from being transmitted to outer housing 238. Outer housing 238 may be similar in shape and construction to housing 12 described hereinabove with reference to FIGS. 1 and 2.

A first pair of resilient strips, such as a first pair of leaf springs 250, is preferably attached to first yoke 204 and to second yoke 220 as shown in FIG. 9. A second pair of resilient strips, such as a second pair of leaf springs 252, is preferably attached to second yoke 220 and to inner housing 236 as shown in FIG. 9.

Figure 10:
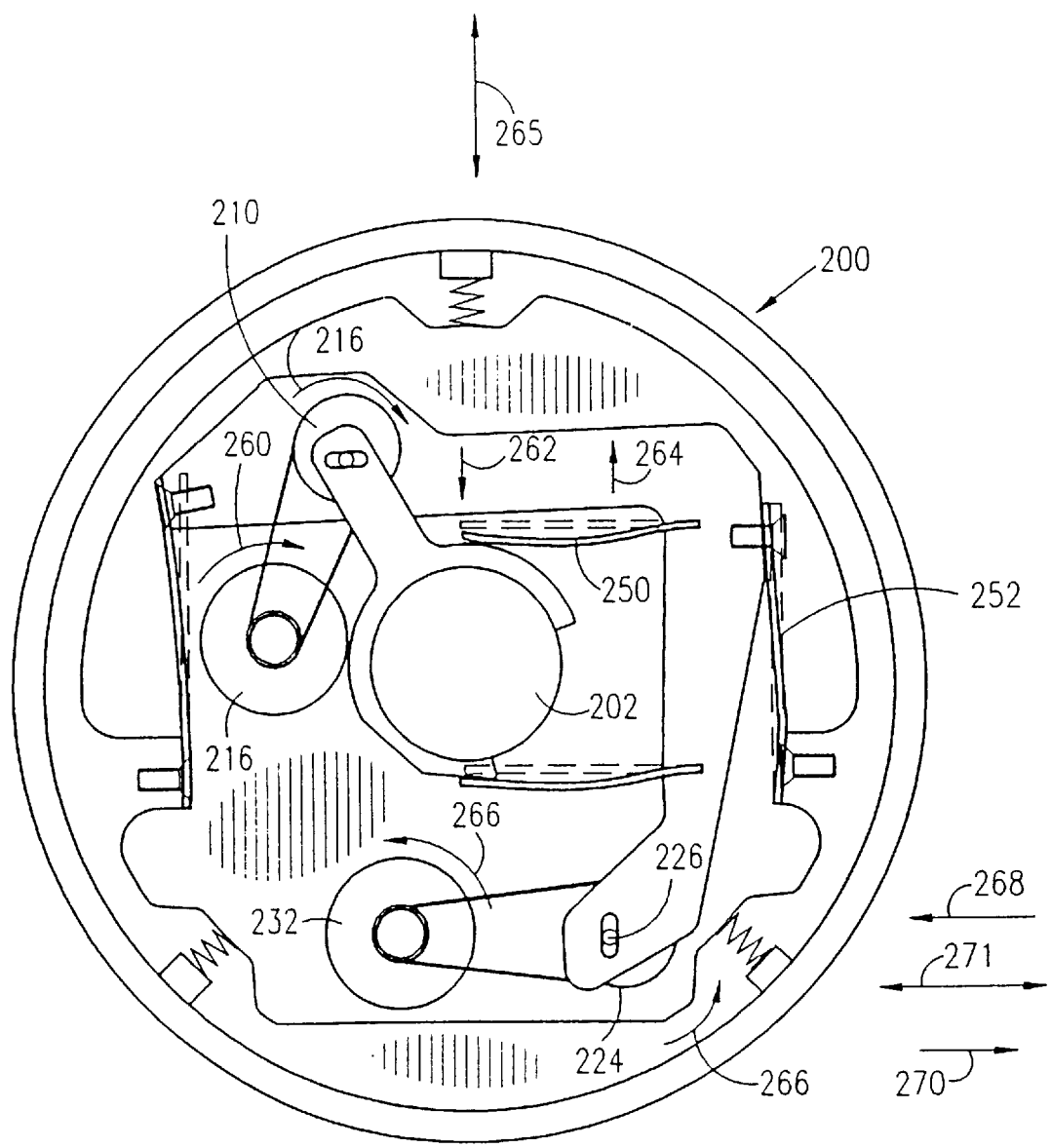

The operation of scanner 200 is now described with reference to FIG. 10. Rotation of motor 216, for example, in the direction of an arrow 260, causes wheel 210 to rotate in the same direction. Rotation of wheel 210 in the direction of arrow 260 causes eccentric pin 212 to move alternately generally in the direction of arrows 262 and 264, generally along an axis 265. The alternate motion of pin 212 imparts a similar motion to lens 202. The motion of lens 202 is restricted and controlled by the resiliency of leaf springs 250.

Rotation of motor 232, for example, in the direction of an arrow 266, causes wheel 224 to rotate in the same direction. Rotation of wheel 224 in the direction of arrow 266 causes eccentric pin 226 to move alternately generally in the direction of arrows 268 and 270, generally along an axis 271 which is generally perpendicular to axis 265. The alternate motion of pin 226 imparts a similar motion to lens 202. The motion of lens 202 is restricted and controlled by the resiliency of leaf springs 252.

Thus, rotation of motors 216 and 232 causes lens 202 to oscillate along one or both of generally mutually perpendicular axes 265 and 271. A laser beam (not shown) passing through lens 202 is deflected according to the oscillations of lens 202, much in the same manner as described hereinabove for scanner 10 with reference to FIGS. 1–5C. The combination of the two generally harmonic motions of lens 202 along the generally mutually perpendicular axes 265 and 271, traces out a Lissajous figure, much in the same manner as described hereinabove with reference to FIGS. 6A–6C.

Figure 11:
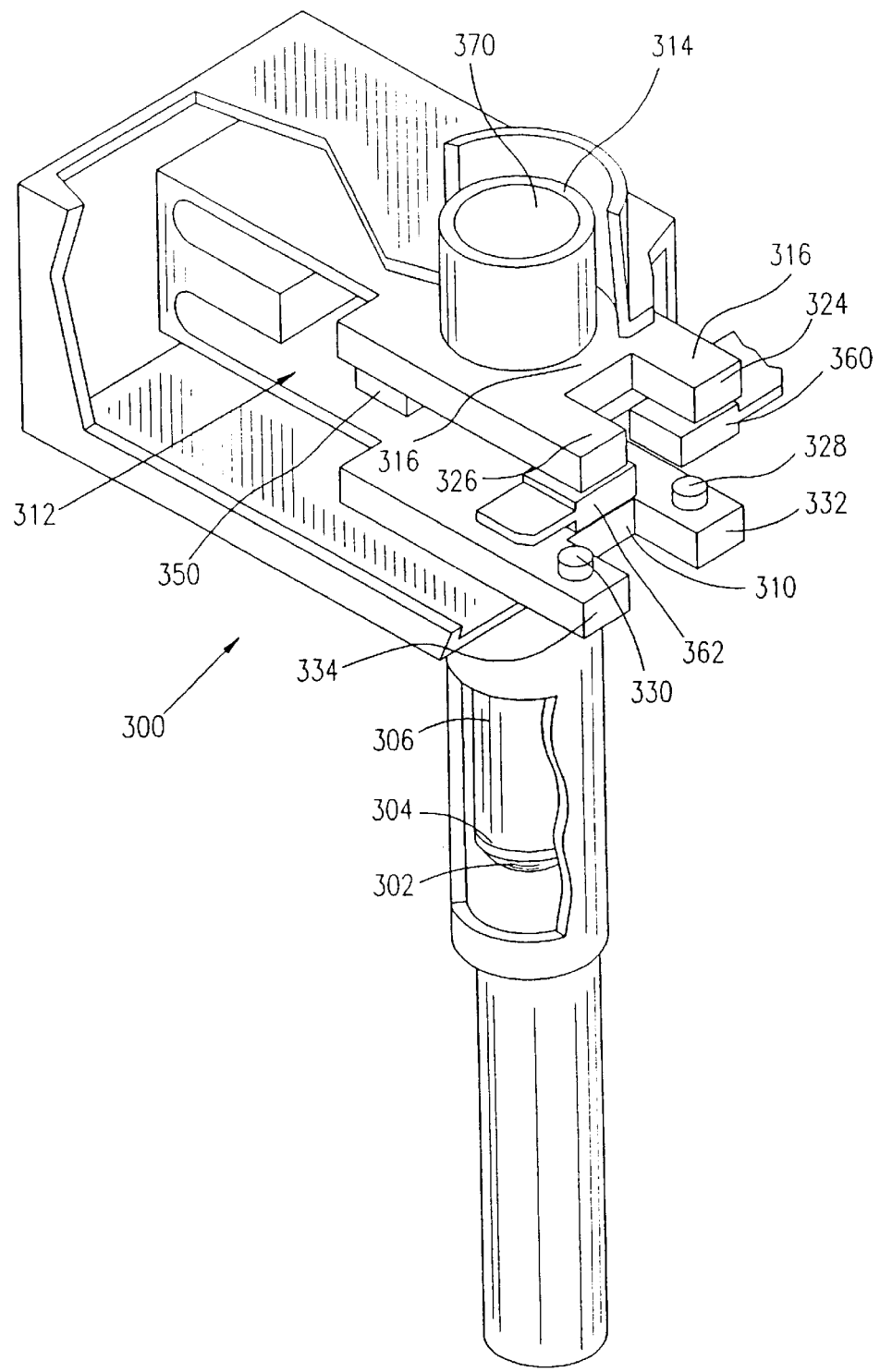
FIGS. 11, 12 and 13 are simplified pictorial, front and side view illustrations, respectively, of a mirrorless scanner, constructed and operative in accordance with still another preferred embodiment of the present invention, in respective oscillating orientations with respect to first and second axes, FIG. 13 being the view taken in the direction of arrow XIII in FIG. 12.
Figure 13:
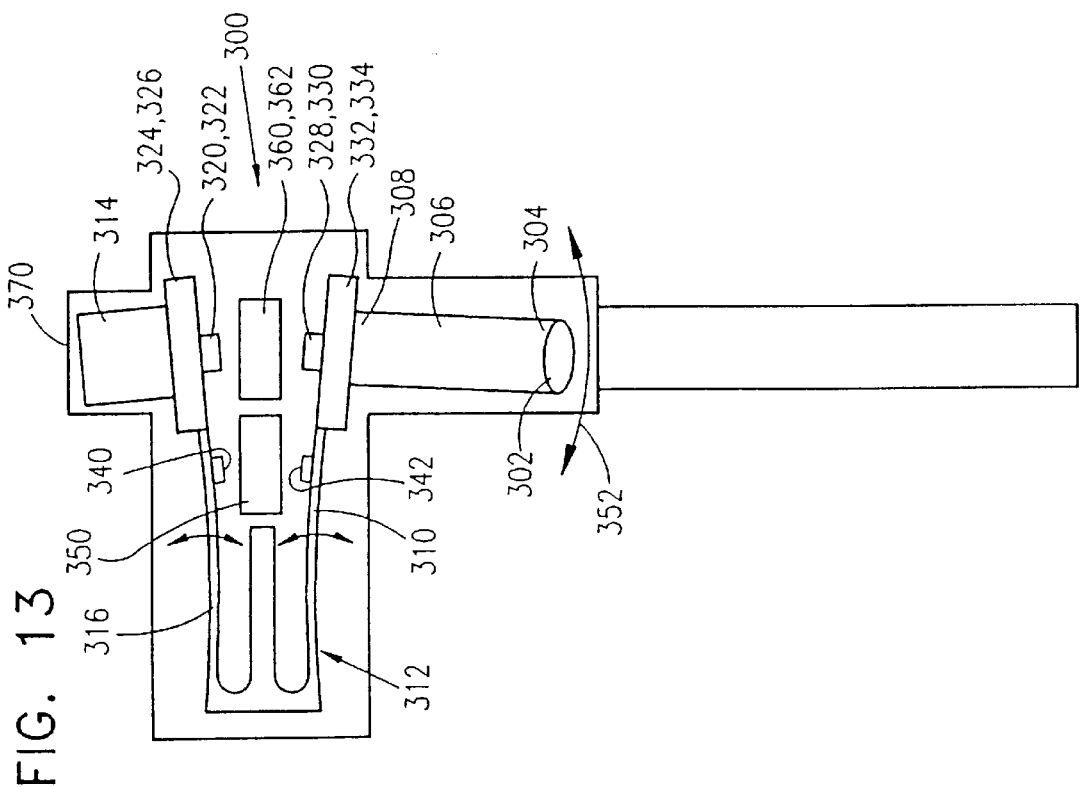
Figure 12:
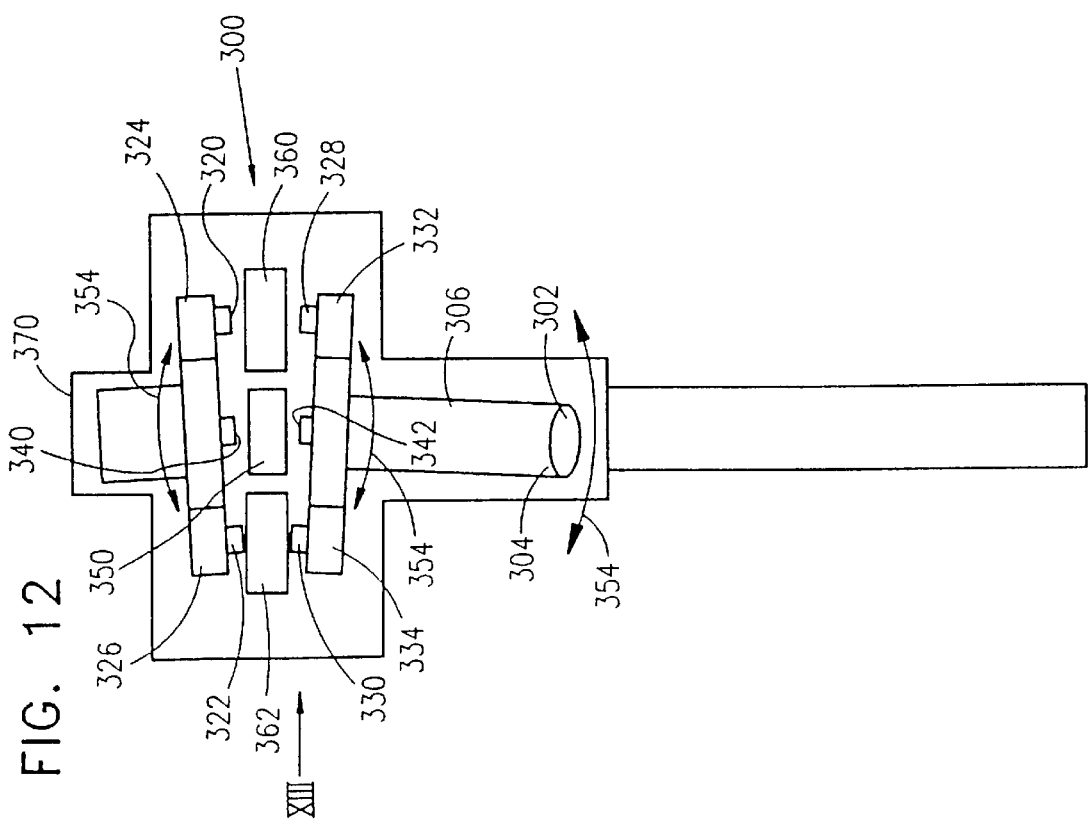

Reference is now made to FIGS. 11, 12 and 13 which are simplified pictorial, front and side view illustrations, respectively, of a mirrorless scanner 300, constructed and operative in accordance with another preferred embodiment of the present invention. Scanner 300 includes a lens 302 preferably attached at an end 304 of a hollow tube 306. An end 308 of tube 306, opposite to end 304, is preferably fixedly attached to a first tine 310 of a flexural fork 312, as seen in FIG. 13. A hollow counterweight 314 is preferably fixedly attached to a second tine 316 of flexural fork 312.

A pair of magnets 320 and 322 are preferably fixedly attached to two bifurcated ends 324 and 326, respectively, of second tine 316, as seen in FIG. 12. A pair of magnets 328 and 330 are preferably fixedly attached to two bifurcated ends 332 and 334, respectively, of first tine 310, as seen in FIG. 12.

A pair of magnets 340 and 342 are preferably fixedly attached to tines 316 and 310, respectively, as seen in FIG. 13.

A first electromagnetic vibration device, such as a solenoid 350, is operative to attract or repel magnets 340 and 342, thereby imparting an oscillatory motion of lens 302 generally in the direction of a double arrow 352, as seen in FIG. 13.

A second electromagnetic vibration device, such as a solenoid 360, is operative to attract or repel magnets 320 and 328, thereby imparting an oscillating motion of lens 302 generally in the direction of a double arrow 354, as seen in FIG. 12. Alternatively, or preferably additionally, a third electromagnetic vibration device, such as a solenoid 362, is operative to attract or repel magnets 322 and 330, thereby imparting an oscillatory motion of lens 302 generally in the direction of double arrow 354, as seen in FIG. 12.

In operation, a laser beam (not shown) enters scanner 300 at an inlet 370, passes first through hollow counterweight 314 and then through lens 302. The laser beam is deflected according to the oscillations of lens 302, much in the same manner as described hereinabove for scanner 10 with reference to FIGS. 1–5C.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited to what has been particularly shown and described hereinabove. Rather, the scope of the present invention is defined only by the claims that follow:

We claim:

1. A mirrorless scanner comprising:
   a hand piece attachable to a source of laser light, said source of laser light producing a laser beam;
   a lens mounted in said hand piece operative to receive the laser beam from the source of laser light and to direct said laser beam onto a target; and
   a vibrator coupled to said lens for vibrating said lens in at least two dimensions for causing said laser beam to scan across the target.

2. A mirrorless scanner according to claim 1 and wherein said vibrator comprises at least two electromagnetic vibration devices, wherein said at least two electromagnetic vibration devices each comprise a magnet attached to said lens and an electromagnet which selectively applies at least one of an attractive and a repulsive magnetic force on said magnet.

3. A mirrorless scanner according to claim 2 and wherein said at least two electromagnetic vibration devices each provide vibration of the lens along a different axis.

4. A mirrorless scanner according to claim 2 and wherein said vibrator is operative to vibrate said lens in at least one of a random and pseudorandom pattern.

5. A mirrorless scanner according to claim 1 and wherein said vibrator comprises at least one electric motor.

6. A mirrorless scanner according to claim 1 and wherein said vibrator comprises at least one solenoid.

7. A mirrorless scanner according to claim 1 and wherein said lens is mounted on a flexure hinge, wherein a first end of said flexure hinge is attached to said lens, and a second end of said flexure hinge, opposite to said first end, is attached to a pair of generally mutually perpendicular flexure joints, each said flexure joint comprising a first pair of slender arms, generally spaced 180° apart, and a second pair of slender arms, generally spaced 180° apart, and oriented generally 90° from said first pair of slender arms, and wherein said flexure hinge has a first mode of vibration comprising a swaying motion about an imaginary axis joining said first pair of slender arms, and a second mode of vibration comprising a swaying motion about an imaginary axis joining said second pair of slender arms.

8. A mirrorless scanner according to claim 1 and comprising a gas port upstream of a tip of said hand piece for flow therethrough of a gas.

9. A scanning method comprising the steps of:
   producing a laser beam outside of a hand piece;
   employing a lens in said hand piece to receive the laser beam and to direct said laser beam onto a target;
   vibrating said lens in at least two dimensions for causing said laser beam to scan across the target.

10. A scanning method according to claim 9 and wherein said vibrating step comprises employing at least two electromagnetic vibration devices.

11. A scanning method according to claim 9 and wherein said vibrating step includes vibration of the lens along two different axes.

12. A scanning method according to claim 9 and wherein said vibrating step vibrates said lens in at least one of a random and pseudorandom pattern.

13. A method according to claim 9 and comprising causing a gas to flow through a tip of said hand piece to help prevent debris from entering said hand piece.

* * * * *